US008216359B2

(12) United States Patent
Lee et al.

(10) Patent No.: US 8,216,359 B2
(45) Date of Patent: Jul. 10, 2012

(54) DELAYED-SETTING CALCIUM PHOSPHATE PASTES

(75) Inventors: Dosuk D. Lee, Scarsdale, NY (US); Youngmi M. Lee, legal representative, Scarsdale, NY (US); Aron D. Rosenberg, Brookline, MA (US); Laurent D. Gilles De Pelichy, Frejus (FR); Manish Sutaria, Watertown, MA (US); Aliassghar N. Tofighi, Waltham, MA (US)

(73) Assignee: ETEX Corporation, Cambridge, MA (US)

( * ) Notice: Subject to any disclaimer, the term of this patent is extended or adjusted under 35 U.S.C. 154(b) by 707 days.

(21) Appl. No.: 11/578,337

(22) PCT Filed: Apr. 14, 2005

(86) PCT No.: PCT/US2005/012583
§ 371 (c)(1),
(2), (4) Date: Dec. 26, 2006

(87) PCT Pub. No.: WO2005/117919
PCT Pub. Date: Dec. 15, 2005

(65) Prior Publication Data
US 2008/0028992 A1    Feb. 7, 2008

Related U.S. Application Data

(60) Provisional application No. 60/562,497, filed on Apr. 15, 2004.

(51) Int. Cl.
*C04B 12/02* (2006.01)
*C04B 28/34* (2006.01)
*C01C 3/08* (2006.01)
*A01N 59/26* (2006.01)
*A61B 17/58* (2006.01)

(52) U.S. Cl. ........ 106/690; 106/691; 423/380; 424/602; 606/92

(58) Field of Classification Search .................. 424/601, 424/602, 57; 106/690, 691; 606/76, 77, 606/86 R, 92; 423/308
See application file for complete search history.

(56) References Cited

U.S. PATENT DOCUMENTS

| | | |
|---|---|---|
| 2,967,802 A | 1/1961 | Towey et al. |
| 3,608,071 A | 9/1971 | Relyveld et al. |
| 3,925,545 A | 12/1975 | Relyveld |
| 4,016,252 A | 4/1977 | Relyveld |
| 4,108,690 A | 8/1978 | Heller |
| 4,110,432 A | 8/1978 | Wilkinson et al. |
| 4,157,378 A | 6/1979 | Tomlinson et al. |
| 4,329,332 A | 5/1982 | Couvreur et al. |
| 4,346,709 A | 8/1982 | Schmitt |
| 4,347,234 A | 8/1982 | Wahlig et al. |
| 4,353,888 A | 10/1982 | Sefton |
| 4,429,691 A | 2/1984 | Niwa et al. |
| 4,609,327 A | 9/1986 | Nishimori |
| 4,612,053 A | 9/1986 | Brown et al. |
| 4,620,327 A | 11/1986 | Caplan et al. |
| 4,684,673 A | 8/1987 | Adachi |
| 4,737,411 A | 4/1988 | Graves, Jr. et al. |
| 4,842,603 A | 6/1989 | Draenert |
| 4,849,193 A | 7/1989 | Palmer et al. |
| 4,880,610 A | 11/1989 | Constantz |
| 4,892,538 A | 1/1990 | Aebischer et al. |
| RE33,161 E | 2/1990 | Brown et al. |
| 4,917,702 A | 4/1990 | Scheicher et al. |
| RE33,221 E | 5/1990 | Brown et al. |
| 4,938,938 A | 7/1990 | Ewers et al. |
| 4,959,104 A | 9/1990 | Iino et al. |
| 5,007,930 A | 4/1991 | Dorman et al. |
| 5,034,059 A | 7/1991 | Constantz |
| 5,037,639 A | 8/1991 | Tung |
| 5,041,138 A | 8/1991 | Vacanti et al. |
| 5,047,031 A | 9/1991 | Constantz |
| 5,053,212 A | 10/1991 | Constantz et al. |
| 5,073,373 A | 12/1991 | O'Leary et al. |
| 5,085,861 A | 2/1992 | Gerhart et al. |
| 5,129,905 A | 7/1992 | Constantz |
| 5,149,368 A | 9/1992 | Liu et al. |
| 5,152,836 A | 10/1992 | Hirano et al. |
| 5,178,845 A | 1/1993 | Constantz et al. |
| 5,197,985 A | 3/1993 | Caplan et al. |
| 5,226,914 A | 7/1993 | Caplan et al. |
| 5,258,044 A | 11/1993 | Lee |
| 5,262,166 A | 11/1993 | Liu et al. |
| 5,281,265 A | 1/1994 | Liu |
| 5,286,763 A | 2/1994 | Gerhart et al. |

(Continued)

FOREIGN PATENT DOCUMENTS

EP    0 268 463    5/1988

(Continued)

OTHER PUBLICATIONS

Aggerbeck and Heron, "Adjuvanticity of Aluminum Hydroxide and Calcium Phosphate in Diptheria-Tetanus Vaccines I," *Vaccine* 13:1360-1365 (1995).
Alper et al. "Osteogenesis in Bone Defects in Rats: The Effects of Hydroxyapatite and Demineralized Bone Matrix," *Am. J. Med. Sci.* 298:371-376 (1989).
Aoki, "Science and Medical Applications of Hydroxyapatite," *JAAS* 11-15 (1991).
Appel et al., "Recent Advances in Implants for Bone Growth Promotion," *Exp. Opin. Ther. Patents* 4:1461-1469 (1994).

(Continued)

*Primary Examiner* — Jerry Lorengo
*Assistant Examiner* — Carlos Barcena
(74) *Attorney, Agent, or Firm* — Clark & Elbing LLP; Todd Armstrong

(57) ABSTRACT

The invention features delayed-setting calcium phosphate pastes which are useful for the preparation of delivery vehicles for biologically active agents, useful for the treatment of orthopedic conditions and can be stored for long periods without prematurely setting.

33 Claims, No Drawings

U.S. PATENT DOCUMENTS

| | | | |
|---|---|---|---|
| 5,290,558 A | 3/1994 | O'Leary et al. |
| 5,306,305 A | 4/1994 | Lee |
| 5,336,264 A | 8/1994 | Constanz et al. |
| 5,342,441 A | 8/1994 | Mandai et al. |
| 5,352,715 A | 10/1994 | Wallace et al. |
| 5,399,665 A | 3/1995 | Barrera et al. |
| 5,443,832 A | 8/1995 | Amerongen et al. |
| 5,462,751 A | 10/1995 | Kossovsky et al. |
| 5,470,803 A | 11/1995 | Bonfield et al. |
| 5,486,359 A | 1/1996 | Caplan et al. |
| 5,496,399 A | 3/1996 | Ison et al. |
| 5,508,342 A | 4/1996 | Antonucci et al. |
| 5,510,396 A | 4/1996 | Prewett et al. |
| 5,514,378 A | 5/1996 | Mikos et al. |
| 5,516,532 A | 5/1996 | Atala et al. |
| 5,522,893 A | 6/1996 | Chow et al. |
| 5,525,148 A | 6/1996 | Chow et al. |
| 5,542,973 A | 8/1996 | Chow et al. |
| 5,543,019 A | 8/1996 | Lee et al. |
| 5,545,254 A | 8/1996 | Chow et al. |
| 5,565,502 A | 10/1996 | Glimcher et al. |
| 5,569,442 A | 10/1996 | Fulmer et al. |
| 5,571,493 A | 11/1996 | Fulmer et al. |
| 5,580,623 A | 12/1996 | Fulmer et al. |
| 5,605,713 A | 2/1997 | Boltong |
| 5,650,176 A | 7/1997 | Lee et al. |
| 5,665,120 A | 9/1997 | Ohtsuka et al. |
| 5,676,976 A | 10/1997 | Lee et al. |
| 5,683,461 A | 11/1997 | Lee et al. |
| 5,683,496 A | 11/1997 | Ison et al. |
| 5,683,667 A | 11/1997 | Fulmer et al. |
| 5,691,397 A | 11/1997 | Glimcher et al. |
| 5,697,981 A | 12/1997 | Ison et al. |
| 5,700,289 A | 12/1997 | Breitbart et al. |
| 5,702,717 A | 12/1997 | Cha et al. |
| 5,709,742 A | 1/1998 | Fulmer et al. |
| 5,763,092 A | 6/1998 | Lee et al. |
| 5,782,971 A | 7/1998 | Constantz et al. |
| 5,783,217 A | 7/1998 | Lee et al. |
| 5,795,330 A | 8/1998 | Tofighi et al. |
| 5,820,632 A | 10/1998 | Constantz et al. |
| 5,843,289 A | 12/1998 | Lee et al. |
| 5,846,312 A | 12/1998 | Ison et al. |
| 5,885,540 A | 3/1999 | Fulmer et al. |
| 5,900,254 A | 5/1999 | Constantz |
| 5,904,716 A | 5/1999 | Gendler |
| 5,952,010 A | 9/1999 | Constantz |
| 5,958,504 A | 9/1999 | Lee et al. |
| 5,962,028 A | 10/1999 | Constantz |
| 5,964,932 A | 10/1999 | Ison et al. |
| 5,968,253 A | 10/1999 | Poser et al. |
| 5,980,482 A | 11/1999 | Tofighi et al. |
| 6,002,065 A | 12/1999 | Constantz et al. |
| 6,005,162 A | 12/1999 | Constantz |
| 6,027,742 A | 2/2000 | Lee et al. |
| 6,030,635 A | 2/2000 | Gertzman et al. |
| 6,033,582 A | 3/2000 | Lee et al. |
| 6,053,970 A | 4/2000 | Ison et al. |
| 6,071,982 A | 6/2000 | Wise et al. |
| 6,117,456 A | 9/2000 | Lee et al. |
| 6,132,463 A | 10/2000 | Lee et al. |
| 6,139,578 A | 10/2000 | Lee et al. |
| 6,214,368 B1 | 4/2001 | Lee et al. |
| 6,277,151 B1 | 8/2001 | Lee et al. |
| 6,287,341 B1 | 9/2001 | Lee et al. |
| 6,331,312 B1 | 12/2001 | Lee et al. |
| 6,334,891 B1 | 1/2002 | Constantz et al. |
| 6,340,477 B1 | 1/2002 | Anderson |
| 6,443,988 B2 | 9/2002 | Felt et al. |
| 6,461,631 B1 | 10/2002 | Dunn et al. |
| 6,464,889 B1 | 10/2002 | Lee et al. |
| 6,485,754 B1 | 11/2002 | Wenz et al. |
| 6,541,037 B1 | 4/2003 | Lee et al. |
| 6,544,290 B1 | 4/2003 | Lee et al. |
| 6,582,470 B1 | 6/2003 | Lee et al. |
| 6,599,516 B1 | 7/2003 | Knaack |
| 6,840,961 B2 | 1/2005 | Tofighi et al. |
| 6,953,594 B2 | 10/2005 | Lee et al. |
| 6,972,130 B1 | 12/2005 | Lee et al. |
| 2002/0076429 A1 | 6/2002 | Wironen et al. |
| 2002/0098222 A1 | 7/2002 | Wironen et al. |
| 2002/0127280 A1* | 9/2002 | Higham ............... 424/602 |
| 2002/0137812 A1 | 9/2002 | Chow et al. |
| 2002/0155137 A1 | 10/2002 | Lee et al. |
| 2002/0155167 A1 | 10/2002 | Lee et al. |
| 2002/0187104 A1 | 12/2002 | Li et al. |
| 2003/0120351 A1 | 6/2003 | Tofighi et al. |
| 2004/0002558 A1 | 1/2004 | McKay |
| 2004/0097612 A1 | 5/2004 | Rosenberg et al. |
| 2004/0127995 A1* | 7/2004 | Shalaby ............... 623/23.58 |
| 2005/0106260 A1 | 5/2005 | Constantz et al. |
| 2005/0147551 A1 | 7/2005 | Tofighi et al. |
| 2005/0260278 A1 | 11/2005 | Constantz et al. |
| 2005/0260279 A1 | 11/2005 | Constantz et al. |
| 2006/0018974 A1 | 1/2006 | Constantz et al. |

FOREIGN PATENT DOCUMENTS

| | | |
|---|---|---|
| EP | 0 347 028 | 12/1989 |
| EP | 0 419 275 | 3/1991 |
| EP | 0 664 133 | 7/1995 |
| JP | 63111875 | 5/1988 |
| JP | 63170205 | 7/1988 |
| JP | 01320251 | 12/1989 |
| JP | 2182261 | 7/1990 |
| JP | 5305134 | 11/1993 |
| JP | 6228011 | 8/1994 |
| JP | 7277712 | 10/1995 |
| JP | 2002-291866 | 10/2002 |
| JP | T 2003-514006 | 4/2003 |
| JP | 2003-180817 | 7/2003 |
| JP | 2004-535232 | 11/2004 |
| JP | T 2006-522614 | 10/2006 |
| WO | WO 92/00109 | 1/1992 |
| WO | WO 92/02453 | 2/1992 |
| WO | WO 94/02412 | 2/1994 |
| WO | WO 94/04657 | 3/1994 |
| WO | WO 94/08458 | 4/1994 |
| WO | WO 94/20064 | 9/1994 |
| WO | WO 94/25080 | 11/1994 |
| WO | WO 95/08319 | 3/1995 |
| WO | WO 96/03160 | 2/1996 |
| WO | WO 96/36562 | 11/1996 |
| WO | WO 97/17285 | 5/1997 |
| WO | WO 98/16209 | 4/1998 |
| WO | WO99/38543 | 8/1999 |
| WO | WO 01/08714 | 2/2001 |
| WO | WO 02/062721 | 8/2002 |
| WO | WO 02/100331 | 12/2002 |
| WO | WO 2004/093734 | 11/2004 |
| WO | WO 2005069837 A2 * | 8/2005 |

OTHER PUBLICATIONS

Atala et al., "Injectable Alginate Seeded with Chondrocytes as a Potential Treatment for Vesicoureteral Reflux," *J. Urol.* 150:745-747 (1993).

Athanasou, "Cellular Biology of Bone-Resorbing Cells," *J. Bone Joint Surg. Am.* 78:1096-1112 (1996).

Attawia et al., "Osteoblast-Like Cell Adherence and Migration Through 3-Dimensional Porous Polymer Matrices," *Biochem. Biophys. Res. Commun* 213:639-644(1995).

Barton et al., "Surface and Bulk Properties of Amorphous Calcium Phosphate," *Surface Chem. Colloids* 87: 379 No. 73954v (1977).

Benghuzzi et al., "Alcap Ceramic Implantable Devices and the Effect of Surface Area on the Delivery of Various Steroid Hormones," 8th Southern Biomedical Engineering Conference, Richmond, VA, Oct. 15-16, 1989; Biomater. Artif. Cells Artif. Organs, 17:463 (1989).

Benghuzzi et al., "Long-Term Delivery of Danazol by Biodegradable Ceramic Devices," 8th Southern Biomedical Engineering Conference, Richmond, VA, Oct. 15-16, 1989; Biomater. Artif. Cells Artif. Organs, 17:463 (1989).

Benghuzzi et al., "Resorbable and Biodegradable Ceramics as Drug Delivery Systems," 8th Southern Biomedical Engineering Conference, Richmond, VA, Oct. 15-16, 1989; Biomater. Artif. Cells. Artif. Organs, 17:463 (1989).

Benghuzzi et al., "Controlled Release of Hydrophilic Compounds by Resorbable and Biodegradable Ceramic Drug Delivery Devices," *Biomed. Sci. Instrum.* 28:179-182 (1992).

Besic et al., "Electron Probe Microanalysis of Noncarious Enamel and Dentin and Calcified Tissues in Mottled Teeth," *J. Dent. Res.* 48:131-139 (1969).

Bonfield, "Chapter 16- Design of Bioactive Ceramic-Polymer Composites," An Introduction to Biometrics, IRC in Biomedical Materials, Queen Mary and Westfield College, London, UK, 16:299-303.

Boskey, "Matrix Proteins and Mineralization: An Overview," *Connect. Tissue Res.* 35:357-363 (1996).

Brown, "Phase Relationships in the Ternary System $CaO-P_2O_5-H_2O$ at 25°C," *J. Am. Ceram. Soc.* 75:17-22 (1992).

Cannon et al., "Continuous Delivery of Azidothymidine by Hydroxyapatite or Tricalcium Phosphate Ceramics," *Biomed. Sci. Instrum.* 31:159-164 (1995).

Chung et al., "Biological Effects of Drug-Loaded Biodegradable Membranes for Guided Bone Regeneration," J. Periodont. Res. 32:172-175 (1997).

Constantz et al., "Skeletal Repair by in Situ Formation of the Mineral Phase of Bone," *Science* 267:1796-1799 (1995).

Covey et al., "Clinical Induction of Bone Repair with Demineralized Bone Matrix or a Bone Morphogenetic Protein," *Orthop. Rev.* 18:857-863 (1989).

Denissen et al., "Net-Shaped Hydroxyapatite Implants for Release of Agents Modulating Periodontal-Like Tissues," *J. Periodontal Res.* 32:40-46(1997).

Driessens et al., "Calcium Phosphate Bone Cements," *Encyc. Hand. Biomat. Bioeng.*, pp. 855-877 (1995).

Ducheyne et al., "Chapter 15: Bioceramic Composites," In Advanced Series in Ceramics-vol. 1: *An Introduction to Bioceramics*, 281-297 (1993).

Eanes et al, "Intermediate States in the Precipitation of Hydroxyapatite," *Nature* 208:365-367 (1965).

Eanes et al. "Intermediate Phases in the Basic Solution Preparation of Alkaline Earth Phosphates," *Chemical Abstracts* 69:10348, No. 110373f (1968).

Eanes, "Thermochemical Studies on Amorphous Calcium Phosphate," *Calcif Tissue Res.* 5:133-145 (1970).

Elgendy et al., "Osteoblast-Like Cell (MC3T3-E1) Proliferation on Bioerodible Polymers: An Approach Towards the Development of a Bone-BioErodible Polymer Composite Material," *Biomater.* 14:263-269 (1993).

Fabbri et al., "Hydroxyapatite-Based Porous Aggregates: Physico-Chemical Nature, Structure, Texture and Architecture," *Biomater.*16: 225-228 (1995).

Fink and Simonsmeier, "Business Laws," *Rem. Pharm. Sci. 17th Ed.* 1890-1891 (1985).

Freed et al., "Cultivation of Cell-Polymer Cartilage Implants in Bioreactors," *J. Cellular Biochemistry* 51:257-264 (1993).

Freed et al., "Biodegradable Polymer Scaffolds for Tissue Engineering," *Biotech.* 12:689-693 (1994).

Gennaro, ed., "Clinical/ Medical Testing," *Rem. Pharm. Sci. 17th Ed.* 39-40 (1985).

Glimcher et al., "Recent Studies of Bone Mineral: Is the Amorphous Calcium Phosphate Theory Valid," *J. Crystal Growth* 53:100-119 (1981).

Glimcher, "Recent Studies of the Mineral Phase in Bone and its Possible Linkage to the Organic Matrix by Protein-Bound Phosphate Bonds," *Philos. Trans. R. Soc. Lond. B.* 304:479-508 (1984).

Glowacki et al., "Demineralized Bone Implants," *Clin. Plast. Surg.* 12:233-241 (1985).

Goto et al., "Studies on the Toxicities of Aluminum Hydroxide and Calcium Phosphate as Immunological Adjuvants for Vaccines," *Vaccine* 11:914-918 (1993).

Goto et al., "Local Tissue Irritating Effects and Adjuvant Activities of Calcium Phosphate and Aluminum Hydroxide with Different Physical Properties," *Vaccine* 15:1364-1371 (1997).

Graves et al., "Resorbable Ceramic Implants," *J. Biomed. Mater. Res. Symposium* 2:91-115 (1971).

Greenfield et al., "Formation Chemistry of Amorphous Calcium Phosphates Prepared from Carbonate Containing Solutions," *Calc. Tiss. Res.* 9:152-162 (1972).

Gupta et al., "Adjuvants—A Balance Between Toxicity and Adjuvanticity," *Vaccine* 11:293-306 (1993).

Gupta et al., "Comparison of Adjuvant Activities of Aluminum Phosphate, Calcium Phosphate and Stearyl Tyrosine for Tetanus Toxoid," *Biologicals* 22:53-63 (1994).

Hirasawa et al., "Manufacture of High Purity Hydroxyapatite," *Chemical Abstracts*, 108:166-167, No. 78193h (1988).

Holmes et al., "Surface Areas by Gas Adsorption on Amorphous Calcium Phosphate and Crystalline Hydroxyapatite," *Calc. Tiss. Res.* 7:163-174 (1971).

Hubbell, "Biomaterials in Tissue Engineering," *Biotech*. 13:565-576 (1995).

Ickovic et al., "Calcium-Phosphate-Adjuvanted Allergens: Total and Specific IgE Levels Before and After Immunotherapy with House Dust and *Dermatophagoides pteronyssinus* Extracts," *Ann. Immunol.* 134D:385-398 (1983).

IJntema et al., "Hydroxyapatite Microcarriers for Biocontroiled Release of Protein Drugs," *Int'l. J. Pharm.* 112:215-224 (1994).

Ikada et al., "Release of Antibiotic from Composites of Hydroxyapatite and Poly(lactic acid)," *J. Control. Release* 2:179-186 (1985).

Ishaug et al., "Osteoblast Function on Synthetic Biodegradable Polymers," *J. Biomed. Mater. Res.* 28:1445-1453 (1994).

Ishikawa et al., "Effects of Preparation Conditions in Aqueous Solution on Properties of Hydroxyapatites," *Chemical Abstracts*, 113: 6001, No. 218168 (1990).

Itokazu et al., "Drug Delivery Systems Using Porous Hydroxyapatite Blocks," *J. Orthop. Surg.* 2:47-50 (1994).

Kato et al., "Relationship Between Hemolytic Activity and Adsorption Capacity of Aluminum Hydroxide and Calcium Phosphate as Immunological Adjuvants for Biologicals," *Microbiol. Immunol.* 38:543-548 (1994).

Knaack et al., "Novel Fully Resorbable Calcium Phosphate Bone Substitute," *1997 ASBMR Abstract*, 12: s202, (1997).

Knaack, "Endothermically Setting Calcium Phosphate Bone Substitute," Orthopaedic Congress, Aug. 20-22, 1997, Boston, MA.

Knaack et al., "A Fully Resorbable Calcium Phosphate Bone Substitute," *Portland Bone Symposium*, pp. 692-701, (1997).

Kossovsky et al., "Surface-Modified Nanocrystalline Ceramics for Drug Delivery Applications," *Biomaterials* 15:1201-1207 (1994).

Kossovsky et al., "Preservation of Surface-Dependent Properties of Viral Antigens Following Immobilization on Particulate Ceramic Delivery Vehicles," *J. Biomed. Mat. Res.* 29:561-573 (1995).

Kreuter et al., "Influence of the Particle Size on the Adjuvant Effect of Particulate Polymeric Adjuvants," *Vaccine* 4:125-129 (1986).

Labarthe et al., "Sur la Structure et les Propriétés des Apatites Carbonatées de Type B Phospho-Calciques," *Ann. Chem.* 8:289-301 (1973).

Mileti et al., "Development of a Hydroxyapatite Ceramic Matrix for the Continuous Delivery of Coumadin," *Biomed. Sci. Instrum.* 31:177-182 (1995).

Moldovan et al., "A Ceramic System for Continuous Release of Acetylsalicylic Acid," *Biomed. Sci. Instrum.* 30:175-180 (1994).

Moldovan et al., "Continuous Delivery of Analgesics by Ceramics," Fifth World Biomaterials Congress, Toronto, Canada, Jun. 2, 1996. (Abstract only).

Norian Corporation, Product Information Sheet, "The Material Science of Norian SRS™, Skeletal Repair System™," (1997).

Nylen et al., "Molecular and Ultrastructural Studies of Non-Crystalline Calcium Phosphates," *Calcif. Tissue Res.* 9:95-108 (1972).

Otsuka et al., "Drug Release Behavior from Self-Setting Calcium Phosphate Cement Containing Anti-Cancer Drug," *Proceed. Intern. Symp. Control. Rel. Bioact. Mater.* 21:268-269 (1994).

Otsuka et al., "A Novel Skeletal Drug Delivery System Using Self-Setting Calcium Phosphate Cement. 4: Effects of the Mixing Solution Volume on the Drug Release Rate of Heterogenous Aspirin-Loaded Cement," *J. Pharm. Sci.* 83:259-263 (1994).

Otsuka et al., "A Novel Skeletal Drug Delivery System Using Self-Setting Calcium Phosphate Cement. 9: Effects of the Mixing Solution Volume on Anticancer Drug Release from Homogeneous Drug-Loaded Cement," *J. Pharm. Sci.* 84:733-736 (1995).

Otsuka et al., "Effect of Particle Size of Metastable Calcium Phosphates on Mechanical Strength of a Novel Self-Setting Bioactive Calcium Phosphate Cement," *J. Biomed. Mater. Res.* 29:25-32 (1995).

Pool, "Coral Chemistry Leads to Human Bone Repair," *Science* 267:1772 (1995).

Posner et al., "Synthetic Amorphous Calcium Phosphate and its Relation to Bone Mineral Structure," *Bone Mineral Structure*, 8: 273-281 (1975).

Redondo et al., "Effect of particulate porous hydroxyapatite on osteoinduction of demineralized bone autografts in experimental reconstruction of the rat mandible," *Int. J. Oral. Maxillofar. Surg.* 24:445-448 (1995).

Relyveld, "Current Developments in Production and Testing of Tetanus and Diptheria Vaccines," *New Developments with Human and Veterinary Vaccines*, pp. 51-76 (1980).

Relyveld et al., "Calcium Phosphate Adjuvanted Allergens," *Annals of Allergy* 54:521-529 (1985).

Relyveld et al., "Preparation and Use of Calcium Phosphate Adsorbed Vaccines," *Develop. Biol. Standard* 65:131-136 (1986).

Relyveld et al, "Humoral Response in Rabbits Immunized with Calcium Phosphate Adjuvanted HIV-1 gp160 Antigen," *Biomed. & Pharmacother*. 48:79-83 (1994).

Rey et al., "The Carbonate Environment in Bone Mineral: A Resolution-Enhanced Fourier Transform Infrared Spectroscopy Study," *Calcif. Tissue Int.* 45:157-164 (1989).

Rey et al., "Structural Studies of the Mineral Phase of Calcifying Cartilage," *J. Bone Miner. Res.* 6:515-525 (1991).

Rey et al., "Preparation of Microporous Ceramic at Low Temperature from Poorly Crystalline Apatite," *Symposium V: Hydroxyapatite and related compounds* (Abstract only) (1993).

Rey et al., "Chemical Properties of Poorly Crystalline Apatites" *Phosphorus Res. Bul*, 6:67-70 (1996). (Abstract only).

Shinto et al., "Calcium Hydroxyapatite Ceramic Used as a Delivery System for Antibiotics," *J. Bone Joint Surg. Br.* 74-B:600-604 (1992).

Shors et al., "Chapter 10: Porous Hydroxyapatite," In *An Introduction to Bioceramics*, eds. Hersch et al., Work Sci. Publ. Co. Pte. Ltd.: 181-198 (1993).

Termine et al., "Amorphous/Crystalline Interrelationships in Bone Mineral," *Calc. Tissue Res*. 1: 8-23 (1967).

Thoma et al., "Biodegradable Gentamicin Depot-Implants Made of Beta-Tricalcium Phosphate Ceramics. 3: In Vivo Studies on Drug Release, Tissue Tolerance, and Biodegradation," *Pharmazie* 46:266-270 (1991) (Abstract only).

Thoma et al., "Biodegradable Controlled Release Implants Based on β-Tricalcium Phosphate Ceramic," *Eur. J. Pharm. Biopharm.* 38:107-112 (1992).

Thomson et al., "Fabrication of Biodegradable Polymer Scaffolds to Engineer Trabecular Bone," *J. Biomater. Sci. Polym. Edn*. 7:23-30 (1995).

Törmälä, "Biodegradable Self-Reinforced Composite Materials; Manufacturing Structure and Mechanical Properties," *Clin. Mater.* 10:29-34 (1992).

Tung et al., "An Intermediate State in Hydrolysis of Amorphous Calcium Phosphate," *Calcif. Tissue Int.*35:783-790 (1983).

Tung, "In Vitro Drug Release of Antibiotic-Loaded Porous Hydroxyapatite Cement," Artif. Cells Blood Substit. Immob. Biotech. 23:81-88 (1995).

Uchida et al., "Slow Release of Anticancer Drugs from Porous Calcium Hydroxyapatite Ceramic," *J. Orthop. Res*. 10:440-445 (1992).

Vassilev, "Aluminium Phosphate But Not Calcium Phosphate Stimulates the Specific IgE Response in Guinea Pigs to Tetanus Toxoid," *Allergy* 33:155-159 (1978).

Yamamura et al., "Antitumor Effects and Distrubutions of Adriamycin Incorporated Into Hydroxyapatite Implants in a Cancer Rat Model Bearing Swarm Rat Chondrosarcoma," *Japan. J. Pharm*. 66:433-438 (1994).

Yamamura et al., "Anticancer Effects of Adriamycin-Loaded Hydroxyapatite Implants Determined in a Swarm Rat Chondrosarcoma Model," *Japan. J. Pharm*. 65:289-291 (1994).

Yasue et al., "Effect of Adsorption of Succinic Acid on the Formation of Amorphous Calcium Phosphate," *J. Ceramic Soc. Japan* (International Edition), 102: 1125-1130 (1994).

Communication from the European Patent Office for EP 05778214.6-1219, mailed Feb. 3, 2009.

Canadian Patent Office Action (CA 2,562,675), dated Nov. 30, 2011.

Bloemers et al., "Autologous Bone Versus Calcium-Phosphate Ceramics in Treatment of Experimental Bone Defects," *J. Biomed. Materials. Res. Part B: Appl. Biomat*. 66B:526-531 (2003).

Symposium of the Japanese Society of Biomaterials, Characteristics and Clinical Application of Bioactive Bone Paste (Calcium Phosphate Cement), p. 26, 2000.

Japanese Office Action (JP 2007-508509) dated May 9, 2012.

\* cited by examiner

DELAYED-SETTING CALCIUM PHOSPHATE PASTES

CROSS-REFERENCE TO RELATED APPLICATIONS

This application claims priority under 35 U.S.C. §371 from international application PCT/US2005/012583, filed Apr. 14, 2005, which claims priority under 35 U.S.C. §119 from U.S. Provisional Patent Application No. 60/562,497, filed Apr. 15, 2004, both of which are incorporated by reference herein.

BACKGROUND OF THE INVENTION

The invention relates to calcium phosphate implants and delivery vehicles for biologically active agents.

In the drug delivery arena, calcium phosphate ceramics have received considerable attention as potential delivery vehicles because of their biocompatibility and their affinity for protein reagents (see, e.g., Ijntema et al, *Int. J. Pharm.* 112:215 (1994); Itokazu et al., *J. Orth. Res.* 10:440 (1992); Shinto et al., *J. Bone Joint Surg.* 74-B:600 (1992); and Uchida et al., *J. Orth. Res.* 10:440 (1992)). Most of these materials have been in the form of prefabricated, sintered hydroxyapatite in either granule or block forms. These preparations have several drawbacks, including a limited ability to conform to skeletal defects, particularly in the case of blocks; inadequate structural integrity of granules (which do not bond together); and difficulty in modeling the implant to the shape of missing skeletal tissue with both blocks and granules. The block form of hydroxyapatite provides structural support, but among other complications, must be held in place by mechanical means, which greatly limits its use and its cosmetic results. Also, it is very difficult to saw a hydroxyapatite block into a shape that fits the patient's individual defect. In general, all of these products are ceramics, produced by high temperature sintering, and are not individually crystalline, but rather have their crystal boundaries fused together. Most ceramic-type materials are in general functionally biologically non-absorbable (having an absorption rate generally not exceeding on the order of 1% per year).

Another type of calcium phosphate composition includes an amorphous, apatitic calcium phosphate as a reactant, a promoter, and an aqueous liquid to form a hardening paste. See, e.g., U.S. Pat. Nos. 5,650,176; 5,676,976; 5,683,461; 6,027,742; and 6,117,456 to Lee et al. This system provides a bioactive ceramic material that is biocompatible, bioresorbable and workable for long periods of time at room temperature. The bioactive ceramic material may be formed at low temperatures, is readily formable and/or injectable, and yet can harden to high strength upon further reaction. The bioactive ceramic material contains poorly crystalline apatitic calcium phosphate solids with calcium-to-phosphate (Ca/P) ratios comparable to naturally occurring bone minerals and having stiffness and fracture roughness similar to natural bone. The bioactive ceramic composite material is strongly bioresorbable and its biosorbability and reactivity can be adjusted to meet the demands of the particular therapy and/or implant site.

The long term storage of calcium phosphate paste is complicated by its hardening over time. Delayed-setting formulations of calcium phosphate pastes are needed to simplify their use and reduce the amount of manipulation required of a physician prior to implantation.

SUMMARY OF THE INVENTION

The invention is based on the discovery that it is possible to prepare delayed-setting calcium phosphate pastes using non-aqueous liquids. The delayed-setting pastes are useful in the preparation of delivery vehicles for biologically active agents and as implants for the treatment of orthopedic conditions.

In a first aspect, the invention features a delayed-setting paste including a calcium phosphate material and a liquid, wherein the liquid includes less than 5% (w/w) water and the paste forms a hardened calcium phosphate material when placed in a moist environment.

The delayed-setting paste is prepared by combining a calcium phosphate material with a liquid including less than 5% (w/w) water. The liquid can include less than 4%, 3%, 2.5%, 2%, 1.5%, 1%, 0.75%, 0.5%, 0.25%, or 0.1% water. Desirably, the liquid includes less than 1% (w/w) water. The delayed-setting paste includes at least 5% (w/w) liquid. Desirably, the delayed-setting paste includes at least 7.5%, 10%, 12.5%, 15%, 17.5%, 20%, 22.5%, 25%, 27.5%, or even 30% (w/w) liquid. Liquids useful in the preparation of the delayed-setting pastes of the invention include, without limitation, dimethyl sulfoxide, N-methyl 2-pyrrolidone, glycofurol, ethyl lactate, ethanol, propylene glycol, 1,2- dimethoxyethane, diglyme, dimethyl isosorbide, SOLKETAL®, tetrahydrofurfuryl alcohol, glycerol, glycerol formal, polyglycerols, triacetin, propylene carbonate, polyethylene glycol, lecithin and other phospholipids, and combinations thereof. Desirably, the liquid includes N-methyl 2-pyrrolidone.

The delayed-setting paste includes at least 30% (w/w) calcium phosphate material. Desirably, the delayed-setting paste includes at least 35%, 40%, 45%, 50%, 55%, 60%, 65%, 70%, 75%, 80%, 85%, or even 90% (w/w) calcium phosphate material. Calcium phosphate materials include, without limitation, calcium metaphosphate, dicalcium phosphate dihydrate, heptacalcium phosphate, tricalcium phosphate dihydrate, crystalline hydroxyapatite (HA), poorly crystalline calcium phosphate (PCA), calcium pyroposphate, monetite, octacalcium phosphate, amorphous calcium phosphate, and mixtures thereof. Desirably, the calcium phosphate material includes amorphous calcium phosphate or a poorly crystalline calcium phosphate.

The delayed-setting pastes of the invention optionally include a supplementary material selected from bioerodible materials (e.g., biodegradable and bioresorbable materials) and non-erodible materials. Bioerodible materials include polysaccharides, nucleic acids, carbohydrates, proteins, polypeptides, poly($\alpha$-hydroxy acids), poly(lactones), poly (amino acids), poly(anhydrides), poly(orthoesters), poly (anhydride-co-imides), poly(orthocarbonates), poly($\alpha$-hydroxy alkanoates), poly(dioxanones), poly(phosphoesters), or copolymers thereof. Desirably, the bioerodible material includes collagen, glycogen, chitin, starch, keratins, silk, demineralized bone matrix, hyaluronic acid, poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), or copolymers thereof. Non-erodible materials include dextrans, celluloses and cellulose derivatives (e.g., methylcellulose, carboxy methylcellulose, hydroxypropyl methylcellulose, and hydroxyethyl cellulose), polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, or copolymers thereof. Bioerodible and non-erodible materials can be selected to introduce porosity or modify physical properties, such as strength and viscosity.

The delayed-setting pastes of the invention optionally include a biologically active agent. Biologically active agents that can be used in the compositions and methods described herein include, without limitation, osteogenic proteins, antibiotics, polynucleotides, anti-cancer agents, growth factors, and vaccines. Osteogenic proteins include, without limitation, BMP-2, BMP-3, BMP-3b, BMP-4, BMP-5, BMP-6, BMP-7, BMP-8, BMP-9, BMP-10, BMP-1 1, BMP-12, BMP-13, BMP-14, BMP-15, BMP-16, BMP-17, and BMP-18. Biologically active agents also include alkylating agents, platinum agents, antimetabolites, topoisomerase inhibitors, antitumor antibiotics, antimitotic agents, aromatase inhibitors, thymidylate synthase inhibitors, demineralized bone matrix, DNA antagonists, farnesyltransferase inhibitors, pump inhibitors, histone acetyltransferase inhibitors, metalloproteinase inhibitors, ribonucleoside reductase inhibitors, TNF alpha agonists, TNF alpha antagonists, endothelin A receptor antagonists, retinoic acid receptor agonists, immuno-modulators, hormonal agents, antihormonal agents, photodynamic agents, and tyrosine kinase inhibitors.

The delayed-setting pastes of the invention optionally include an effervescent agent. Effervescent agents include, without limitation, sodium bicarbonate. The delayed-setting paste may include, for example, from about 1 to about 40 percent (w/w) sodium bicarbonate.

The delayed-setting pastes of the invention optionally include inert agents, such as a salt or a sugar, which are provided to act as pore-forming constituents of the composition. Preferably, the salt or sugar comprises about 0-80% by volume of the composition. In other embodiments, the salt or sugar comprises about 0-50% by volume, more preferably 0-30% by volume, most preferably about 25% by volume.

The invention also features a method of preparing a vehicle for the delivery of a biologically active agent. The method includes the steps of (i) preparing a delayed-setting paste including a calcium phosphate material, a biologically active agent, and a liquid, wherein the liquid includes less than 5% (w/w) water, and (ii) placing the paste in a moist environment until a hardened calcium phosphate material is formed. Desirably, the delayed-setting paste further includes a supplementary material.

The invention further features a method of preparing an implant. The method includes the steps of (i) preparing a delayed-setting paste including a calcium phosphate material and a liquid, wherein the liquid includes less than 5% (w/w) water, and (ii) placing the paste in a moist environment until a hardened calcium phosphate material is formed. Desirably, the delayed-setting paste further includes a supplementary material.

In any of the above methods, the delayed-setting paste can be hardened by implantation into a mammal (i.e., the moist environment is inside a mammal).

The invention features a method of promoting bone growth at a site in need thereof. The method includes the step of applying a delayed-setting paste of the invention to the site, e.g., the surface of an orthopedic implant, or the site of a bone fracture. Desirably, the paste includes a biologically active agent, such as an osteogenic protein.

The invention also features a method of preparing a structural support for segmented bone. The method includes the step of contacting bone segments with a delayed-setting paste of the invention. The method optionally includes contacting fixation hardware (e.g., screws and/or plates) with the delayed-setting paste.

The invention further features a kit including (i) a delayed-setting paste of the invention, and (ii) instructions for implanting the delayed-setting paste into a mammal. The delayed-setting paste optionally includes a biologically active agent.

The invention also features a method of promoting investment in a company conducting or planning in vivo studies on a delayed-setting paste described herein. The method includes the step of disseminating information about the identity, therapeutic use, toxicity, efficacy, or projected date of governmental approval of the delayed-setting paste.

The invention features a method for promoting the use of a delayed-setting paste described herein. The method includes the step of disseminating information about the identity or therapeutic use of the delayed-setting paste.

As used herein "identity" refers to an identifier, such as a structure, diagram, figure, chemical name, common name, tradename, formula, reference number, or any other label that conveys the composition of a delayed-setting paste of the invention to another.

By "in vivo studies" is meant any study in which a delayed-setting paste of the invention is administered to a living mammal, including, without limitation, non-clinical studies, e.g., to collect data concerning toxicity and efficacy, as well as clinical studies.

By "projected date of governmental approval" is meant any estimate of the date on which a company will receive approval from a governmental agency to sell, e.g., to patients, doctors, or hospitals, a composition including a delayed-setting paste of the invention. A governmental approval includes, for example, the approval of a new drug application by the United States Food and Drug Administration, among others.

As used herein, "hardening" or "setting" refers to the process by which the delayed-setting paste of the invention is placed in a moist environment and transformed into a hardened calcium phosphate material, e.g., hydroxyapatite (HA) or poorly crystalline apatitic (PCA) calcium phosphate. The calcium phosphate material is considered to be "hardened" or "set" when it is a substantially non-formable solid. Such a hardened calcium phosphate material has a minimal compressibility of at least 1 MPa, desirably at least 2, 3, 4, 5, 6, 7, 8, 9, 10, 12, 14, 16, 18, or even 20 MPa, and tends to undergo plastic as opposed to elastic deformation.

By "moist environment" is meant an environment having an amount of water sufficient to cause the paste to harden at 37° C. within 24 hours. Examples of moist environments include those in which the paste is in contact with biological fluids or distilled water.

As used herein, "non-aqueous" refers to liquids containing less than 5% (w/w) water. Desirably, the non-aqueous liquids contain less than 4%, 3%, 2.5%, 2%, 1.5%, 1%, 0.75%, 0.5%, 0.25%, or even 0.1% water. The calcium phosphate material may include hydrates, such as dicalcium phosphate dihydrate (DCPD, $CaHPO_4.H_2O$) or amorphous calcium phosphate (ACP, $Ca_3(PO_4)_2.nH_2O$, n=3-4.5). The water associated with hydrates in the paste is complexed to the calcium phosphate material and does not contribute to the water content of the non-aqueous liquid. The water content of the non-aqueous liquid can be determined by first filtering the liquid from the calcium phosphate material, followed by Karl-Fischer titration to determine the percentage of water in the liquid.

As used herein "paste" refers to a flowable or deformable delayed-setting calcium phosphate material which has not hardened. Pastes of the invention can be designed to have any one of a variety of consistencies. For example, increasing the proportion of non-aqueous liquid can produce a paste which fails to hold its shape, but is more easily injected via a syringe. A putty-like consistency is achieved by reducing the proportion of non-aqueous liquid.

As used herein, "biocompatible" refers to a material that does not elicit a substantial immune response in the host. There is always concern, when a foreign object is introduced into a living body, that the object will induce an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., *Int. J. Pharm.* 112:215 (1994)).

By "bioresorbable" is meant the ability of a material to be resorbed or remodeled in vivo. The resorption process involves degradation and elimination of the original implant material through the action of body fluids, enzymes or cells. The resorbed materials may be used by the host in the formation of new tissue, or it may be otherwise re-utilized by the host, or it may be excreted.

The invention features delayed-setting calcium phosphate pastes and their use in the preparation of delivery vehicles for biologically active agents and for the preparation of orthopedic implants. The pastes can be stored for long periods of time without setting.

Other features and advantages of the invention will be apparent from the following Detailed Description and the claims.

DETAILED DESCRIPTON

We have made delayed-setting calcium phosphate pastes which are useful for the preparation of vehicles for the delivery of biologically active agents and for the treatment of orthopedic conditions.

The pastes of the invention include a calcium phosphate material and a non-aqueous liquid and upon hydration form a hardened calcium phosphate material. Optionally, the pastes include a biologically active agent, supplementary material, effervescent agent, bioresorbable solid elements, or combinations thereof.

Calcium Phosphate Materials

The calcium phosphate component of the invention may be any biocompatible, calcium phosphate material known in the art. The calcium phosphate material may be produced by any one of a variety of methods and using any suitable starting components. For example, the calcium phosphate material may include amorphous, apatitic calcium phosphate. Calcium phosphate material may be produced by solid-state acid-base reaction of crystalline calcium phosphate reactants to form crystalline hydroxyapatite solids. Other methods of making calcium phosphate materials are known in the art, some of which are described below.

Poorly Crystalline Apatitic (PCA) Calcium Phosphate

The calcium phosphate material can be poorly crystalline apatitic (PCA) calcium phosphate. PCA material is described in application U.S. Pat. Nos. 5,650,176; 6,214,368; 6,287,341; and 6,541,037, each of which is incorporated herein by reference.

The PCA material is characterized by its biological resorbability, biocompatibility, and its minimal crystallinity. Its crystalline character is substantially the same as natural bone. Using the compositions and methods of the invention, the PCA material is implanted as a precursor delayed-setting paste. Implantation exposes the paste to physiological conditions (e.g., moisture and body heat), resulting in a conversion to PCA as the material hardens in place.

Generally, the PCA material hardens in less than five hours, and substantially hardens in about one to five hours, under physiological conditions. Preferably, the material is substantially hardened within about 10-30 minutes. The hardening rate under physiological conditions, may be varied according to the therapeutic need by modifying a few simple parameters as described in U.S. Pat. No. 6,027,742, which is incorporated herein by reference.

The conversion reaction that produces the PCA material may be initiated prior to implantation by adding distilled water to a mixture of the delayed-setting precursor paste to form a hydrated precursor, which is then implanted. For example, a shaped or molded delayed-setting precursor paste can be soaked in distilled water, for example, to remove much of the non-aqueous liquid prior to implantation. Other aqueous agents such as buffers, saline, serum or tissue culture medium may be used in place of distilled water. Alternatively, the delayed-setting paste can be implanted without any prior hydration, e.g., with a 16 gauge needle, into the patient where the delayed-setting paste is hydrated in vivo.

Most often, the resulting bioresorbable calcium phosphate material will be "calcium deficient," with a calcium to phosphate ratio of less than about 1.6 as compared to the ideal stoichiometric value of approximately 1.67 for hydroxyapatite.

Suitable PCA materials may be identified by combining the PCA precursors with one or more non-aqueous liquids or gels to form a paste and allowing the delayed-setting paste to harden into a PCA material. Desirable precursors are capable of hardening in a moist environment, at or around body temperature in less than 5 hours and preferably within 10-30 minutes. Components which harden in this way may then be placed in or adjacent to a bony defect (e.g., intramuscularly or subcutaneously) in a test animal and checked for biological resorbability. Desirable materials are those that, when implanted as a 1-5 g pellet, are at least 80% resorbed within one year. Preferably, the material can be fully resorbed.

The PCA material may be formed in a reaction that employs at least one amorphous calcium phosphate (ACP) precursor, and preferably employs an activated or reactive ACP (see, e.g., PCT application No. WO 98/16209; Examples 1-4). In some instances, the reaction may employ only one precursor ACP, which is converted in a controlled fashion in part or whole to the PCA material. Also, a non-participating promoter may be employed to facilitate conversion of the activated ACP to the PCA material.

The conversion of ACP to PCA material is promoted in the presence of water. Using the methods and compositions of the invention, the ACP is provided as a powder and combined with any other reactants (e.g., a second calcium phosphate), and a non-aqueous liquid to form a delayed-setting paste. This delayed-setting precursor paste is then exposed to moisture, either before or after implantation, and then hardens. The hardening is associated with formation of the PCA material. The conversion of ACP to PCA calcium phosphate proceeds in a controlled fashion and can be used in dental, orthopedic, drug delivery, or other therapeutic applications.

Crystalline Hydroxyapatite

Alternatively, the calcium phosphate material can be crystalline hydroxyapatite (HA). Crystalline HA is described, for example, in U.S. Pat. Nos. Re. 33,221 and Re. 33,161. These patents teach preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described in U.S. Pat. Nos. 5,053,212 and 5,129,905. This calcium phosphate material is produced by solid-state acid-base reaction of crystalline calcium phosphate reactants to form crystalline hydroxyapatite solids.

Crystalline HA materials (commonly referred to as dahllite) may be prepared such that they are flowable, moldable, and capable of hardening in situ (see U.S. Pat. No. 5,962,028). These HA materials (commonly referred to as carbonated hydroxyapatite) can be formed by combining the reactants with a non-aqueous liquid to provide a substantially uniform mixture, shaping the mixture as appropriate, and allowing the mixture to harden in the presence of water (e.g., before or after implantation). During hardening, the mixture crystallizes into a solid and essentially monolithic apatitic structure.

The reactants will generally consist of a phosphate source, e.g., phosphoric acid or phosphate salts, substantially free of water, an alkali earth metal, particularly calcium, source, optionally crystalline nuclei, particularly hydroxyapatite or calcium phosphate crystals, calcium carbonate, and a physiologically acceptable lubricant, such as any of the non-aqueous liquids described herein. The dry ingredients may be pre-prepared as a mixture and subsequently combined with the non-aqueous liquid ingredients under conditions where substantially uniform mixing occurs.

For any of the delayed-setting calcium phosphate pastes described herein, the various components may be combined, mixed, and stored without setting or hardening for weeks, months, or years, depending upon the combination, the water content of the paste, and the storage conditions.

Non-Aqueous Liquids

Non-aqueous liquids suitable for making the pastes of the invention are biocompatible and are at least miscible in aqueous medium, body fluid, or water. Preferably, the non-aqueous liquid is preferably at least moderately soluble, or even very soluble at all concentrations in aqueous medium, body fluid, or water. A liquid that is at least moderately soluble in aqueous or body fluid will allow water to permeate into the paste over a period of time ranging from seconds to weeks, causing the paste to harden, for example into PCA. The slightly soluble liquids will slowly diffuse from the flowable paste and typically will enable the transformation over a period of days to weeks, e.g., about a day to several weeks. The highly soluble liquids will diffuse from the flowable paste over a period of seconds to hours so that hardening begins almost immediately. The non-aqueous liquid preferably is a polar aprotic or polar protic liquid. The liquid can have a molecular weight in the range of about 30 to about 5,000. Preferably, the liquid has a molecular weight in the range of about 30 to about 1000.

Examples of biocompatible non-aqueous liquids that may be used to form the delayed-setting pastes of the invention include aliphatic, aryl, and arylalkyl linear, cyclic and branched organic compounds that are liquid or at least flowable at ambient and physiological temperature and contain such functional groups as alcohols, ketones, ethers, amides, esters, carbonates, sulfoxides, sulfones, and any other functional group that is compatible with living tissue.

Biocompatible, water-miscible liquids include N-methyl-2-pyrrolidone, 2-pyrrolidone; C1 to C15 alcohols, diols, triols and tetraols such as ethanol, glycerine, polyglycerol, propylene glycol, butanol; C3 to C15 alkyl ketones such as acetone, diethyl ketone and methyl ethyl ketone; C3 to C15 esters such as methyl acetate, ethyl acetate, ethyl lactate; C1 to C15 amides such as dimethylformamide, dimethylacetamide and caprolactam; C3 to C20 ethers such as tetrahydrofuran, or SOLKETAL®; tweens, triacetin, propylene carbonate, decylmethylsulfoxide, dimethyl sulfoxide, oleic acid, and 1-dodecylazacycloheptan-2-one. Other preferred solvents are benzyl alcohol, benyl benzoate, dipropylene glycol, tributyrin, ethyl oleate, glycofural, isopropyl myristate, isopropyl palmitate, oleic acid, polyethylene glycol, propylene carbonate, and triethyl citrate.

Polyoxyethylene-polyoxypropylene block copolymers may be used as non-aqueous liquids in the pastes of the invention. These are available under various trade names, including one or more of Synperonic PE series (ICI), Pluronic® series (BASF), Lutrol (BASF), Supronic, Monolan, Pluracare, and Plurodac. The generic term for these polymers is "poloxamer" (CAS 9003-11-6). These polymers have the formula I:

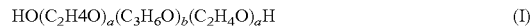

$$HO(C_2H4O)_a(C_3H_6O)_b(C_2H_4O)_aH \quad (I)$$

where "a" and "b" denote the number of polyoxyethylene and polyoxypropylene units, respectively. These copolymers are available in molecular weights ranging from 1000 to 15000 daltons, and with ethylene oxide/propylene oxide ratios between 0.1 and 0.8 by weight. Formulations of rifalazil according to the invention may include one or more of the polyoxyethylene-polyoxypropylene block copolymers above. Formulations of the invention may include one or more of the polyoxyethylene-polyoxypropylene block copolymers above.

Polyethylene glycol sorbitan fatty acid esters may be used may be used as non-aqueous liquids in the pastes of the invention. Examples of commercially available polyethylene glycol sorbitan fatty acid esters include: PEG-10 sorbitan laurate (LIPOSORB® L-10, Lipo Chem.), PEG-20 sorbitan monolaurate (TWEEN ® 20, Atlas/ICI), PEG-4 sorbitan monolaurate (TWEEN® 21, Atlas/ICI), PEG-80 sorbitan monolaurate (Hodag PSML-80, Calgene), PEG-6 sorbitan monolaurate (NIKKOL® GL-1, Nikko), PEG-20 sorbitan monopalmitate (TWEEN® 40, Atlas/ICI), PEG-20 sorbitan monostearate (TWEEN® 60, Atlas/ICI), PEG-4 sorbitan monostearate (TWEEN® 61, Atlas/ICI), PEG-8 sorbitan monostearate (DACOL MSS, Condea), PEG-6 sorbitan monostearate (NIKKOL® TS106, Nikko), PEG-20 sorbitan tristearate (TWEEN® 65, Atlas/ICI), PEG-6 sorbitan tetrastearate (NIKKOL® GS-6, Nikko), PEG-60 sorbitan tetrastearate (NIKKOL® GS-460, Nikko), PEG-5sorbitan monooleate (TWEEN® 81, Atlas/ICI), PEG-6 sorbitan monooleate (NIKKOL® TO-106, Nikko), PEG-20 sorbitan monooleate (TWEEN® 80, Atlas/ICI), PEG-40 sorbitan oleate (Emalex ET 8040, Nihon Emulsion), PEG-20 sorbitan trioleate (TWEEN® 85, Atlas/ICI), PEG-6 sorbitan tetraoleate (NIKKOL® GO-4, Nikko), PEG-30 sorbitan tetraoleate (NIKKOL® GO430, Nikko), PEG-40 sorbitan tetraoleate (NIKKOL® GO-440, Nikko), PEG-20 sorbitan monoisostearate (TWEEN® 120, Atlas/ICI), PEG sorbitol hexaoleate (Atlas G-1086, ICI), polysorbate 80 (TWEEN® 80, Pharma), polysorbate 85 (TWEEN® 85, Pharma), polysorbate 20 (TWEEN® 20, Pharma), polysorbate 40 (TWEEN® 40, Pharma), polysorbate 60 (TWEEN® 60, Pharma), and PEG-6 sorbitol hexastearate (NIKKOL® GS-6, Nikko). Pastes of the invention may include one or more of the polyethylene glycol sorbitan fatty acid esters above.

Desirably, the non-aqueous liquid is selected from dimethyl sulfoxide (DMSO), N-methyl 2-pyrrolidone (NMP), glycofurol, ethyl lactate, ethanol, propylene glycol (PG), 1,2-dimethoxyethane (DME), diglyme, dimethyl isosorbide (DMI), SOLKETAL® tetrahydrofurfuryl alcohol (THFA), glycerin, glycerol, glycerol formal (GF), polyglycerols, triacetin, propylene carbonate, polyethylene glycol (PEG) of various molecular weights, such as PEG 300, PEG 400, and PEG 600, and combinations thereof, because of their biocompatibility.

Supplementary Materials

Composite delayed-setting pastes may be prepared by combining the calcium phosphate material and non-aqueous liquid with a selected supplementary material. The supplementary material is selected based upon its compatibility with calcium phosphate and the other components and its ability to impart properties (biological, chemical, physical, or mechanical) to the composite, which are desirable for a particular therapeutic purpose or for post-sterilization stability. For example, the supplementary material may be selected to improve tensile strength and hardness, increase fracture toughness, and provide imaging capability of the paste after implantation, hydration, and hardening. Furthermore, the supplementary material may be selected to improve the setting time and/or alter flow properties of the delayed-setting paste. The supplementary materials are desirably biocompatible. The supplementary material may also be selected as a cohesiveness agent.

The supplementary material may be added to the calcium phosphate composition in varying amounts and in a variety of physical forms, dependent upon the anticipated therapeutic use. For example, the supplementary material may be in the form of solid structures, such as sponges, meshes, films, fibers, gels, filaments or particles, including microparticles and nanoparticles. The supplementary material itself may be a composite. The supplementary material may be a particulate or liquid additive or doping agent which is intimately mixed with the calcium phosphate material. For example, the supplementary material may be dissolved in the non-aqueous liquid prior to mixing with the calcium phosphate material. When intimately mixed with a calcium phosphate material, the supplementary material may interfere on a macroscopic level with the cementing reaction, but is not present in an amount sufficient to prevent hardening or setting of the paste when placed in a moist environment. The proportions of calcium phosphate material, non-aqueous liquid, and supplementary material can be varied to produce pastes of desired consistency, workability and adherence.

In many instances, it is desirable that the supplementary material be bioresorbable. Bioresorbable material for use as supplementary material in the pastes of the invention include, without limitation, polysaccharides, nucleic acids, carbohydrates, proteins, polypeptides, poly($\alpha$-hydroxy acids), poly (lactones), poly(amino acids), poly(anhydrides), poly (orthoesters), poly (anhydride-co-imides), poly (orthocarbonates), poly($\alpha$-hydroxy alkanoates), poly (dioxanones), and poly(phosphoesters). Preferably, the bioresorbable polymer is a naturally occurring polymer, such as collagen, glycogen, chitin, starch, keratins, silk, demineralized bone matrix, and hyaluronic acid; or a synthetic polymer, such as poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), or copolymers thereof. Such polymers are known to bioerode and are suitable for use in the pastes of the invention. In addition, bioresorbable inorganic supplementary materials, such as compositions including $SiO_2$, $Na_2O$, $CaO$, $P_2O_5$, $Al_2O_3$ and/or $CaF_2$, may be used, as well as salts, e.g., NaCl, and sugars, e.g., mannitol, and combinations thereof.

Supplementary materials may also be selected from non-resorbable or poorly resorbable materials. Suitable non-resorbable or poorly resorbable materials for use in the pastes of the invention include, without limitation, dextrans, cellulose and derivatives thereof (e.g., methylcellulose, carboxy methylcellulose, hydroxypropyl methylcellulose, and hydroxyethyl cellulose), polyethylene, polymethylmethacrylate (PMMA), carbon fibers, poly(ethylene glycol), poly(ethylene oxide), poly(vinyl alcohol), poly(vinylpyrrolidone), poly (ethyloxazoline), poly(ethylene oxide)-co-poly(propylene oxide) block copolymers, poly(ethylene terephthalate)polyamide, and lubricants, such as polymer waxes, lipids and fatty acids.

Biologically Active Agents

The pastes of the invention are useful for the preparation of delivery vehicles for biologically active agents. In general, the only requirement is that the substance remain active within the paste during fabrication or be capable of being subsequently activated or re-activated, or that the biologically active agent be added at the time of implantation of the delayed-setting paste into a host or following hardening of the vehicle at 37° C. in an aqueous environment.

Biologically active agents that can be incorporated into the delivery vehicles of the invention include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be loaded into a delivery vehicle of the invention include, without limitation, anti-cancer agents, antibiotics, analgesics, anti-inflammatory agents, immunosuppressants, enzyme inhibitors, antihistamines, anti-convulsants, hormones, muscle relaxants, anti-spasmodics, ophthalmic agents, prostaglandins, anti-depressants, anti-psychotic substances, trophic factors, osteoinductive proteins, growth factors, and vaccines.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelin A receptor antagonists, retinoic acid receptor agonists, immuno-modulators, hormonal and antihormonal agents, photodynamic agents, and tyrosine kinase inhibitors.

Any of the biologically active agents listed in Table 1 can be used.

TABLE 1

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |

TABLE 1-continued

| | | |
|---|---|---|
| Platinum agents | cisplatin | carboplatinum |
| | oxaliplatin | ZD-0473 (AnorMED) |
| | spiroplatinum, | lobaplatin (Aeterna) |
| | carboxyphthalatoplatinum, | satraplatin (Johnson Matthey) |
| | tetraplatin | BBR-3464 (Hoffmann-La Roche) |
| | ormiplatin | SM-11355 (Sumitomo) |
| | iproplatin | AP-5280 (Access) |
| Antimetabolites | azacytidine | tomudex |
| | gemcitabine | trimetrexate |
| | capecitabine | deoxycoformycin |
| | 5-fluorouracil | fludarabine |
| | floxuridine | pentostatin |
| | 2-chlorodeoxyadenosine | raltitrexed |
| | 6-mercaptopurine | hydroxyurea |
| | 6-thioguanine | decitabine (SuperGen) |
| | cytarabin | clofarabine (Bioenvision) |
| | 2-fluorodeoxy cytidine | irofulven (MGI Pharma) |
| | methotrexate | DMDC (Hoffmann-La Roche) |
| | idatrexate | ethynylcytidine (Taiho) |
| Topoisomerase inhibitors | amsacrine | rubitecan (SuperGen) |
| | epirubicin | exatecan mesylate (Daiichi) |
| | etoposide | quinamed (ChemGenex) |
| | teniposide or mitoxantrone | gimatecan (Sigma-Tau) |
| | irinotecan (CPT-11) | diflomotecan (Beaufour-Ipsen) |
| | 7-ethyl-10-hydroxy-camptothecin | TAS-103 (Taiho) |
| | topotecan | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | BBR-3576 (Novuspharma) | KW-2170 (Kyowa Hakko) |
| Antitumor antibiotics | dactinomycin (actinomycin D) | amonafide |
| | doxorubicin (adriamycin) | azonafide |
| | deoxyrubicin | anthrapyrazole |
| | valrubicin | oxantrazole |
| | daunorubicin (daunomycin) | losoxantrone |
| | epirubicin | bleomycin sulfate (blenoxane) |
| | therarubicin | bleomycinic acid |
| | idarubicin | bleomycin A |
| | rubidazone | bleomycin B |
| | plicamycinp | mitomycin C |
| | porfiromycin | MEN-10755 (Menarini) |
| | cyanomorpholinodoxorubicin | GPX-100 (Gem Pharmaceuticals) |
| | mitoxantrone (novantrone) | |
| Antimitotic agents | paclitaxel | SB 408075 (GlaxoSmithKline) |
| | docetaxel | E7010 (Abbott) |
| | colchicine | PG-TXL (Cell Therapeutics) |
| | vinblastine | IDN 5109 (Bayer) |
| | vincristine | A 105972 (Abbott) |
| | vinorelbine | A 204197 (Abbott) |
| | vindesine | LU 223651 (BASF) |
| | dolastatin 10 (NCI) | D 24851 (ASTAMedica) |
| | rhizoxin (Fujisawa) | ER-86526 (Eisai) |
| | mivobulin (Warner-Lambert) | combretastatin A4 (BMS) |
| | cemadotin (BASF) | isohomohalichondrin-B (PharmaMar) |
| | RPR 109881A (Aventis) | ZD 6126 (AstraZeneca) |
| | TXD 258 (Aventis) | PEG-paclitaxel (Enzon) |
| | epothilone B (Novartis) | AZ10992 (Asahi) |
| | T 900607 (Tularik) | IDN-5109 (Indena) |
| | T 138067 (Tularik) | AVLB (Prescient NeuroPharma) |
| | cryptophycin 52 (Eli Lilly) | azaepothilone B (BMS) |
| | vinflunine (Fabre) | BNP-7787 (BioNumerik) |
| | auristatin PE (Teikoku Hormone) | CA-4 prodrug (OXiGENE) |
| | BMS 247550 (BMS) | dolastatin-10 (NIH) |
| | BMS 184476 (BMS) | CA-4 (OXiGENE) |
| | BMS 188797 (BMS) | |
| | taxoprexin (Protarga) | |
| Aromatase inhibitors | aminoglutethimide | exemestane |
| | letrozole | atamestane (BioMedicines) |
| | anastrazole | YM-511 (Yamanouchi) |
| | formestane | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | mafosfamide (Baxter International) |
| | glufosfamide (Baxter International) | apaziquone (Spectrum Pharmaceuticals) |
| | albumin + 32P (Isotope Solutions) | O6 benzyl guanine (Paligent) |
| | thymectacin (NewBiotics) | |
| | edotreotide (Novartis) | |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |

TABLE 1-continued

| | | |
|---|---|---|
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | |
| | adenocarcinoma vaccine (Biomira) | ISF-154 (Tragen) |
| | CTP-37 (AVI BioPharma) | cancer vaccine (Intercell) |
| | IRX-2 (Immuno-Rx) | norelin (Biostar) |
| | PEP-005 (Peplin Biotech) | BLP-25 (Biomira) |
| | synchrovax vaccines (CTL Immuno) | MGV (Progenics) |
| | melanoma vaccine (CTL Immuno) | β-alethine (Dovetail) |
| | p21 RAS vaccine (GemVax) | CLL therapy (Vasogen) |
| Hormonal and antihormonal agents | estrogens | prednisone |
| | conjugated estrogens | methylprednisolone |
| | ethinyl estradiol | prednisolone |
| | chlortrianisen | aminoglutethimide |
| | idenestrol | leuprolide |
| | hydroxyprogesterone caproate | goserelin |
| | medroxyprogesterone | leuporelin |
| | testosterone | bicalutamide |
| | testosterone propionate; | flutamide |
| | fluoxymesterone | octreotide |
| | methyltestosterone | nilutamide |
| | diethylstilbestrol | mitotane |
| | megestrol | P-04 (Novogen) |
| | tamoxifen | 2-methoxyestradiol (EntreMed) |
| | toremofine | arzoxifene (Eli Lilly) |
| | dexamethasone | |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |
| Tyrosine Kinase Inhibitors | imatinib (Novartis) | kahalide F (PharmaMar) |
| | leflunomide (Sugen/Pharmacia) | CEP-701 (Cephalon) |
| | ZD1839 (AstraZeneca) | CEP-751 (Cephalon) |
| | erlotinib (Oncogene Science) | MLN518 (Millenium) |
| | canertinib (Pfizer) | PKC412 (Novartis) |
| | squalamine (Genaera) | phenoxodiol ( ) |
| | SU5416 (Pharmacia) | trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide,p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, nonsteroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, nor-binaltorphimine, buprenorphine, chlomaltrexamine, funaltrexamine, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

Osteogenic Proteins

The biologically active agent is desirably selected from the family of proteins known as the transforming growth factors-beta (TGF-β) superfamily of proteins, which includes the activins, inhibins and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins which may be useful as the active agent in the paste of the invention include Vgr-2, Jones et al., *Mol. Endocrinol.* 6:1961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention may be BIP, disclosed in WO94/01557; HP00269, disclosed in JP Publication number: 7-250688; and BMP-14 (also known as MP52, CDMP1, and GDF5), disclosed in PCT application WO93/16099. The disclosures of all of the above applications are incorporated herein by reference. A subset of BMPs which are presently preferred for use in the invention include BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18. The active agent is most preferably BMP-2, the sequence of which is disclosed in U.S. Pat. No. 5,013,649, the disclosure of which is incorporated herein by reference. Other osteogenic agents known in the art can also be used, such as teriparatide (Forteo™), Chrysalin®, prostaglandin E2, or LIM protein, among others.

The biologically active agent may be recombinantly produced, or purified from a protein composition. The active agent, if a TGF-β such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-.beta.1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference.

The active agent may further include additional agents such as the Hedgehog, Frazzled, Chordin, Noggin, Cerberus and Follistatin proteins. These families of proteins are generally described in Sasai et al., Cell 79:779-790 (1994) (Chordin); PCT Patent Publication WO94/05800 (Noggin); and Fukui et al., *Devel. Biol.* 159:131 (1993) (Follistatin). Hedgehog proteins are described in WO96/16668; WO96/17924; and WO95/18856. The Frazzled family of proteins is a recently discovered family of proteins with high homology to the extracellular binding domain of the receptor protein family known as Frizzled. The Frizzled family of genes and proteins is described in Wang et al., *J. Biol. Chem.* 271:4468-4476 (1996). The active agent may also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are hereby incorporated by reference herein.

The amount of osteogenic protein effective to stimulate increased osteogenic activity of present or infiltrating progenitor or other cells will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Biologically active agents can be introduced into the delivery vehicle of the invention during or after its formation. Agents may conveniently be mixed into the paste prior to setting. Alternatively, the vehicle may be shaped and hardened and then exposed to the therapeutic agent in solution. This particular approach is particularly well suited for proteins, which are known to have an affinity for apatitic materials. A buffer solution containing the biologically active agent may be employed, instead of water, as the aqueous solution in which the delayed-setting paste is, for example, irrigated prior to implantation. Buffers may be used in any pH range, but most often will be used in the range of 5.0 to 8.0 in preferred embodiments the pH will be compatible with prolonged stability and efficacy of the desired therapeutic agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for it's biocompatibility with the host tissues and its compatibility with the therapeutic agent. For most applications of nucleic acids, peptides or antibiotics a simple phosphate buffered saline will suffice.

Standard protocols and regimens for delivery of the above-listed agents are known in the art. Typically, these protocols are based on oral or intravenous delivery. Biologically active agents are introduced into the vehicle in amounts that allow delivery of an appropriate dosage of the agent to the implant site. In most cases, dosages are determined using guidelines known to practitioners and applicable to the particular agent in question. The exemplary amount of biologically active agent to be included in the paste of the invention or added to the hardened delivery vehicle is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent.

Modification of Delivery Kinetics

One advantage of the delivery vehicles of the invention is that the rate of resorption of the delivery vehicle can be modulated by varying the components of the delayed-setting precursor paste. Pastes that lead to a dense, hardened crystalline product will generally result in a slower resorption time of the implanted vehicle in vivo. There are a variety of ways to alter the density or resorption kinetics of the hardened product. These include adjustment of the volume of non-aqueous liquid used to create the paste, alteration of grain size of the starting calcium phosphate materials, and compression of the paste during hardening.

Leachable or biodegradable particles or materials may be incorporated into the paste. The leachable or biodegradable materials may subsequently be removed (e.g., by leaching) from the hardened material in vivo, so that a highly porous implant is produced. The pastes can include a bioresorbable solid elements having a greater resorption rate in vivo than the implanted and hardened paste. As a result, the hardened implant can be design to produce channels or pores of a preselected size and shape. The result is an increase in porosity and surface area which can be used to modulate the rate of calcium phosphate resorption and rate of release of biologically active agent from the implant. Desirably, the solid elements are insoluble in the non-aqueous liquid used in the preparation of the paste. The solid elements can be selected from rods, fibers, sheets, fibrous mats, star-shapes, and jack-shapes. The elements can include, without limitation, any of the supplementary materials described herein. Desirably, the element is a sugar, inorganic salt, or carbohydrate. Further examples of solid elements are described in U.S. Pat. No. 6,599,516, incorporated herein by reference.

Effervescent Agents

Granulation is desirable to facilitate cell migration and infiltration for secretion of extracellular bone matrix, and to provide access for vascularization. Granules also provide high surface area for enhanced resorption and release of active substance, as well as increased cell-matrix interaction.

A highly porous or even granular implant can be achieved by addition of an effervescent agent to the paste. The effervescent agent may be a gas which is dissolved in the pastes prior to implantation. The gas may be dissolved in the paste under pressure, i.e., by subjecting the composite material to a pressurized atmosphere of the gas, but which is inert to the cementing reaction. The gas is then liberated upon exposure to physiological temperatures (i.e., upon injection or implantation), due to the decrease in gas solubility with increased temperature. Under these circumstances, the gas dissolution and subsequent granulation occurs only during hardening in vivo, and not prior to administration. This is especially attractive since granulation is not desired to occur at room temperature in the syringe. Suitable gases include, without limitation, carbon dioxide, air, nitrogen, helium, oxygen, and argon. Alternatively, the effervescent agent is a solid material which liberates gas upon dissolution. For example, sodium bicarbonate evolves carbon dioxide gas as it converts to an unstable carbonic acid intermediate, which subsequently evolves carbon dioxide and water. Desirably, the sodium carbonate is present in the delayed-setting paste in an amount between 0.5 and 40% (w/w). A more detailed description of the use of effervescent agents is found in U.S. Ser. No. 10/160,607, entitled "Calcuim phosphate delivery vehicles for osteoinductive proteins," filed May 31, 2002.

Porosity can alternatively be achieved by combining an effervescent agent with a cohesiveness agent.

Implantation

The pastes of the invention can be used in the preparation of vehicles to deliver biologically active agents to any of a variety of sites in a mammalian body, preferably in a human body. The delivery vehicles can be implanted subcutaneously, intramuscularly, intraperitoneally, at bony sites, and into ocular areas.

Such vehicles offer the advantage of controlled, localized delivery. As a result, less biologically active agent is required to achieve a therapeutic result in comparison to systemic administration, reducing the potential for side effects maximizing the agent's activity at the site of implantation.

The delivery vehicle can be injected or implanted into any acceptable tissue. Oral formulations are also considered within the scope of the invention. Preferred delivery sites include sites in bone, muscle, the spinal cord, the central nervous system, the intraperitoneal cavity, subcutaneous locations, and the vitreous and aqueous humor of the eye. When the delivery vehicle is delivered to a site under circumstances where vehicle migration is a concern, anchoring sutures or hooks may be incorporated into the vehicle so that it can be attached and maintained in position. When appropriate, the delivery vehicle may be anchored by insertion into a bony site (see below). Particular applications and preferred delivery sites are discussed in more detail below.

Bone

The delivery vehicle has particular advantages for delivery of biologically active agents to sites in bone. Implantation of the delivery vehicle to a bony site includes either anchoring the vehicle to a bone or to a site adjacent to, though not strictly speaking "within", the bone.

Naturally-occurring bone mineral is made of nanometer-sized, poorly-crystalline calcium phosphate with apatitic structure. However, unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae, $Ca_{8.3}(PO_4)_{4.3}(HPO_4, CO_3)_{1.7}(OH, CO_3)_{0.3}$.

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. And because bone tissues undergo constant tissue repair regulated by the mineral-resorbing cells (osteoclasts) and mineral-producing cells (osteoblasts), solubility behavior of minerals is important in maintaining a delicate metabolic balance between these cells activities.

Some of the delivery vehicles described herein are ideal for implantation at bony sites. These vehicles are made from a material that is prepared as a nano-size, poorly crystalline solid with a Ca/P ratio comparable to that of natural bone minerals. The material can be bioresorbable, can be produced at low temperatures, and is readily formable and injectable.

Furthermore, the pastes described herein can be implanted to support bone growth so that it is eventually replaced by the patient's own bone. It should be borne in mind, however, that bone ingrowth may well affect the resorbability rate of the drug delivery for pastes incorporating a biologically active agent. Accordingly, it may be desirable in certain circumstances (e.g., where the biologically active agent must be delivered according to a precise, predetermined administrative schedule) to reduce bone growth into the drug delivery vehicle, for example by blocking penetration of osteocytic or chondrocytic cells or precursors. In most circumstances, ossification can be avoided by placing the device at some distance away from bone. Generally, 1 mm will be sufficient, although greater distances are preferred. Also, compounds such as Indian hedgehog gene and gene products, parathyroid hormone-related protein (PTHRP) and PTHRP receptor agonists may be included in, on, or adjacent to the drug delivery device in order prevent bone growth.

Promoting Ossification

To optimize ossification, the delayed-setting paste or the hardened calcium phosphate composition may be seeded with bone forming cells, such as progenitor cells, stem cells, and/or osteoblasts. This is most easily accomplished by placing the paste or hardened composition in contact with a source of the patient's own bone forming cells. Such cells may be found in bone-associated tissue, blood or fluids, including exogenous fluids which have been in contact with bone or bone materials or regions, including the periosteum, cancellous bone or marrow. When used in conjunction with devices such as screws and pins, the introduction of which into bone is accompanied by breach of the periosteum and/or bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Bone forming cells harvested from the patient may be introduced into the graft to augment ossification. Other steps may also be taken to augment ossification, including introduction bone forming cells harvested from the patient into the graft, or incorporation of trophic factors or bone growth inducing proteins into, or onto the device. Non-autologous bone cells can also be used to promote bone regeneration. Immunosuppressants may be administered to the device recipient, either systemically or by incorporation into the device. Thus, cells or tissues obtained from primary sources, cell lines or cell banks may be used.

See, U.S. Pat. No. 6,132,463 to Lee et al., which is incorporated herein by reference.

Certain categories of biologically active agents are expected to be particularly suitable for delivery to bony sites. For example, where the drug delivery vehicle is applied to a damaged bone site, it may be desirable to incorporate bone regenerative proteins (BRPs) into the vehicle. BRPs have been demonstrated to increase the rate of bone growth and to accelerate bone healing (see, for example, Appel et al., *Exp. Opin. Ther. Patents* 4:1461 (1994)). Exemplary BRPs include, but are in no way limited to, Transforming Growth Factor-Beta (TGF-.beta.), Cell-Attachment Factors (CAFs), Endothelial Growth Factors (EGFs), OP-1, and Bone Morphogenetic Proteins (BMPs). Such BRPs are currently being developed by Genetics Institute, Cambridge, Mass.; Genentech, Palo Alto, Calif.; and Creative Biomolecules, Hopkinton, Mass. Bone regenerative proteins and trophic factors can also be used to stimulate ectopic bone formation if desired. For example, a delayed-setting paste containing BMP-2 can be placed subcutaneously, and bone formation will occur within 2-4 weeks.

Antibiotics and antiseptics are also desirably delivered to bony sites using the delayed-setting pastes of the invention. For example, one of the major clinical implications arising from bone-graft surgery is a need to control the post-operative inflammation or infection, particularly infection associated with osteomyelitis. A drug delivery device of the invention that includes an antibiotic can be used as, or in conjunction with, an improved bone graft to reduce the chances of local infection at the surgery site, contributing to infection-free, thus faster, bone healing process. The efficacy of antibiotics is further enhanced by controlling the resorption of the poorly crystalline hydroxyapatite such that it dissolves at a rate that delivers antibiotic peptides or its active component at the most effective dosage to the tissue repair site. Antibiotics and bone regenerating proteins may be incorporated together into a delayed-setting paste of the invention, to locally deliver most or all of the components necessary to facilitate optimum conditions for bone tissue repair.

Other biologically active agents that are desirably delivered to bony sites include anti-cancer agents, for example for treatment of bone tumors (see, for example, Otsuka et al., *J. Pharm. Sci.* 84:733 (1995)). The delivery vehicles of the invention are useful, for example, where a patient has had a bone tumor surgically removed, because the delayed-setting paste can be implanted to improve the mechanical integrity of the bone site while also treating any remaining cancer cells to avoid metastasis. Exemplary anti-cancer agents include many of the biologically active agents listed in Table 1.

Additional biologically active agents can be incorporated into the delayed-setting paste of the invention for delivery to bony sites include agents that relieve osteoporosis. For example, amidated salmon calcitonin has been demonstrated to be effective against osteoporosis.

Vitamin D and Vitamin K are also desirably delivered to bony sites, as are angiogenic factors such as VEGF, which can be used when it is desirable to increase vascularization.

Orthopedic Uses

The pastes of the invention can be useful for repairing a variety of orthopedic conditions. The delayed-setting paste of the invention may be injected into the vertebral body for treatment of spinal fractures, injected into long bone or flat bone fractures to augment the fracture repair or to stabilize the fractured fragments, or injected into intact osteoporotic bones to improve bone strength. It can be useful in the augmentation of a bone-screw or bone-implant interface. Additionally, it can be useful as bone filler in areas of the skeleton where bone may be deficient. Examples of situations where such deficiencies may exist include post-trauma with segmental bone loss, post-bone tumor surgery where bone has been excised, and after total joint arthroplasty. The paste can be used to hold and fix artificial joint components in patients undergoing joint arthroplasty, as a strut to stabilize the anterior column of the spine after excision surgery, as a structural support for segmented bone (e.g., to assemble bone segments and support screws, external plates, and related internal fixation hardware), and as a bone graft substitute in spinal fusions.

The delayed-setting paste can be used to coat prosthetic bone implants. For example, where the prosthetic bone implant has a porous surface, the delayed-setting paste may be applied to the surface to promote bone growth therein (i.e., bone ingrowth). The paste may also be applied to a prosthetic bone implant to enhance fixation within the bone.

The delayed-setting pastes of the invention are easy to apply and can be readily modeled to accurately reconstruct bony cavities, missing bone, and to recreate contour defects in skeletal bone. The delayed-setting paste can be applied, for example, with a spatula, can be molded and sculpted, and can hold its shape satisfactorily until set.

Subcutaneous

The delivery vehicles can be implanted in non-bony sites, where the device will resorb without ossification. Subcutaneous placement of the delivery vehicle is particularly useful for systemic administration of biologically active compounds. The administration of estrogens and/or progesterones for the used in fertility control is an example of a subcutaneous application. Additionally, the administration of antigens and/or vaccines may be accomplished through subcutaneous implantation.

Central nervous system

The delivery of therapeutic substances to the central nervous system may be accomplished with the inventive delivery vehicles. Useful therapeutic substances include the delivery of γ-aminobutyric acid to epileptic foci, the delivery of L-dopa or dopamine in the striatum or substantia nigra for the treatment of Parkinson's disease, the delivery of growth factors for the prevention of neural degeneration such as GDNF in the lateral ventricles, striatum or substantia nigra for the treatment of Parkinson's disease, the administration of NGF to cortical and other regions for the treatment of Alzheimer's disease, or the administration of CNTF to the sacral or lumbar spinal cord for the treatment of amyotrophic lateral sclerosis (ALS).

The paste of the invention can be packaged in a variety of ways, including, without limitation, in a jar, as a tube which fits within the chamber of a delivery gun, e.g., in the same way as a tube of caulk is placed in a household caulk gun, as a squeezable tube, e.g., in the same way as a tube of toothpaste, as a pre-filled syringe, and as individually wrapped preformed shapes. The desired mode of packaging and delivery of the paste will depend upon the condition to be treated.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Preparation of Calcium Phosphate Cement (CPC)

Amorphous calcium phosphate (ACP) and dicalcium phosphate dihydrate (DCPD) powders were poured into a ceramic jar in equal amounts. The ceramic jar containing the powders and 5000 g milling media (10-mm YTZ) was ball-milled for 3 hours at 100 rpm. The resultant powder was sieved through a 120 mesh screen.

EXAMPLE 2

Preparation of Polymer Containing Non-aqueous Solvent 1.0 g of poly(D,L-lactide-co-glyocolide), Resomer RG 755, was dissolved in 5 mL of 1-methyl-2-pyrrolidinone (also known as methyl pyrrolidone, NMP) solvent. 2.0 g of Poly(D,L-lactide), Resomer R208, was dissolved in 5 mL of NMP.

EXAMPLE 3

Preparation of CPC and Resomer LR708 Composite Powder 0.95 g CPC from Example 1 was mixed with 0.05 g poly(L-lactide-co-D,L-lactide), Resomer LR708, using a spatula.

EXAMPLE 4

Preparation of CPC and Resomer RG755 NMP Paste 1.0 g CPC powder from Example 1 was mixed with 300 μL of NMP solution containing Resomer RG755. The mixture was kneaded thoroughly for one minute to form a paste. The paste was transferred into a syringe.

EXAMPLE 5

Preparation of CPC and Resomer R208 NMP Paste 1.0 g CPC powder from Example 1 was mixed with 350 μL of NMP solution containing Resomer R208. The mixture was kneaded thoroughly for one minute to form a paste. The paste was transferred into a syringe.

EXAMPLE 6

Preparation of CPC-NMP Paste

Powder mixture from Example 3 was mixed with 400 μL of NMP solvent. The mixture was kneaded thoroughly for one minute to form a paste. The paste was transferred into syringe. The powder of Example 1 was treated in the same fashion to produce a paste without a supplementary material.

EXAMPLE 7

Preparation of CPC Pastes Using Aqueous Medium 1.0 g CPC powder from Example 1 was mixed with 400 μL of saline. The mixture was kneaded thoroughly for one minute to form a paste. The paste was transferred into syringe.

EXAMPLE 8

Hardening Characterization of Various Pastes

The hardening of various pastes was characterized by filling pastes into stainless steel molds and incubating at 37° C. for 24 hours. After incubation for a prescribed time, the hardened pellets were removed from molds and subjected to compression testing. The results of paste forming and compression strength measurements are shown in Table 2. The results show similar hardening behavior of CPC pastes with addition of non-aqueous liquid and polymers as when a CPC paste is formed using saline.

TABLE 2

Paste Forming and Compression Strength Measurements

| Powder | Solvent | Physical Aspect of CPC Paste | Compression strength, MPa |
|---|---|---|---|
| Aqueous Formulation | | | |
| CPC | saline | Putty like paste | 30 |
| Non-Aqueous Formulations | | | |
| CPC | NMP | Putty like paste | 28 |
| CPC + Resomer LR 708 | NMP | Putty like paste | 28 |
| CPC | Resomer RG755 dissolved in NMP | Putty like paste | 25 |
| CPC | Resomer R208 dissolved in NMP | Putty like paste, slightly sticky | 25 |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A paste comprising a calcium phosphate material in an amount of at least 55% (w/w) and a non-aqueous liquid, in an amount of 5% to 20% (w/w), selected from dimethyl sulfoxide, N-methyl 2-pyrrolidone, glycofurol, ethyl lactate, ethanol, 1,2-dimethoxyethane, diglyme, dimethyl isosorbide, tetrahydrofurfuryl alcohol, triacetin, propylene carbonate, lecithin, and combinations thereof, wherein said paste comprises less than 5% (w/w) water and said paste forms a hardened poorly crystalline apatitic (PCA) calcium phosphate material when said non-aqueous liquid diffuses from said paste.

2. The paste of claim 1, said paste comprising less than 1% (w/w) water.

3. The paste of claim 2, said paste comprising at least 10% (w/w) of said non-aqueous liquid.

4. The paste of claim 1, wherein said calcium phosphate material is calcium metaphosphate, dicalcium phosphate dihydrate, heptacalcium phosphate, tricalcium phosphate dihydrate, crystalline hydroxyapatite (HA), poorly crystalline calcium phosphate (PCA), calcium pyroposphate, monetite, octacalcium phosphate, amorphous calcium phosphate, or mixtures thereof.

5. The paste of claim 4, wherein said calcium phosphate material comprises a poorly crystalline calcium phosphate.

6. The paste of claim 4, wherein said calcium phosphate material comprises amorphous calcium phosphate.

7. The paste of claim 6, said paste comprising 20% (w/w) of said non-aqueous liquid, wherein said paste comprises less than 1% (w/w) water.

8. The paste of claim 1, wherein said liquid comprises N-methyl 2-pyrrolidone.

9. The paste of claim 1, further comprising a supplementary material.

10. The paste of claim 9, wherein said supplementary material comprises a bioerodible polymer selected from the group consisting of a polysaccharide, nucleic acid, carbohydrate, protein, polypeptide, poly(α-hydroxy acid), poly(lactone), poly(amino acid), poly(anhydride), poly(orthoester), poly(anhydride-co-imide), poly(orthocarbonate), poly(α-hydroxy alkanoate), poly(dioxanone), and poly(phosphoester), and mixtures thereof.

11. The paste of claim 10, wherein said supplementary material comprises a bioerodible material selected from the group consisting of collagen, glycogen, chitin, starch, keratins, silk, demineralized bone matrix, hyaluronic acid, poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), and poly(caprolactone), and mixtures thereof.

12. The paste of claim 9, wherein said supplementary material comprises a non-erodible material selected from the group consisting of dextran, cellulose, polyethylene, polymethylmethacrylate, carbon fiber, poly(ethylene glycol), poly(ethylene oxide), poly(vinyl alcohol), poly(vinylpyrrolidone), poly(ethyloxazoline), poly(ethylene oxide)-co-polypropylene oxide) block copolymer, and poly(ethylene terephthalate)polyamide, and mixtures thereof.

13. The paste of claim 12, wherein said cellulose is methylcellulose, carboxy methylcellulose, hydroxypropyl methylcellulose, or hydroxyethyl cellulose.

14. The paste of claim 1, further comprising a biologically active agent.

15. The paste of claim 14, wherein said biologically active agent is an osteogenic protein, antibiotic, polynucleotide, anti-cancer agent, growth factor, or vaccine.

16. The paste of claim 15, wherein said osteogenic protein is BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, or BMP-18.

17. The paste of claim 14, wherein said biologically active agent is an alkylating agent, platinum agent, antimetabolite, topoisomerase inhibitor, antitumor antibiotic, antimitotic agent, aromatase inhibitor, thymidylate synthase inhibitor, DNA antagonist, farnesyltransferase inhibitor, pump inhibitor, histone acetyltransferase inhibitor, metalloproteinase inhibitor, ribonucleoside reductase inhibitor, TNF alpha agonist, TNF alpha antagonist, endothelin A receptor antagonist, retinoic acid receptor agonist, immuno-modulator, hormonal agent, antihormonal agent, photodynamic agent, or tyrosine kinase inhibitor.

18. The paste of claim 1, further comprising an effervescent agent.

19. The paste of claim 18, wherein said effervescent is sodium bicarbonate.

20. The paste of claim 19, wherein said paste is from about 1 to about 40 percent (w/w) sodium bicarbonate.

21. A kit comprising:
(i) the paste of claim 1, and
(ii) instructions for implanting said paste into a mammal.

22. The kit of claim 21, wherein said paste further comprises a biologically active agent.

23. A method of preparing an implant, comprising:
(i) preparing a paste comprising a calcium phosphate material in an amount of at least 55% (w/w) and a non-aqueous liquid in an amount of 5% to 20% (w/w), wherein said non-aqueous liquid is selected from dimethyl sulfoxide, N-methyl 2-pyrrolidone, glycofurol, ethyl lactate, ethanol, 1,2- dimethoxyethane, diglyme, dimethyl isosorbide, tetrahydrofurfuryl alcohol, triacetin, propylene carbonate, lecithin, and combinations thereof and wherein said paste comprises less than 5% (w/w) water, and
(ii) allowing said paste to form a hardened poorly crystalline apatitic (PCA) calcium phosphate material when said non-aqueous liquid diffuses from said paste.

24. The method of claim 23, wherein said paste further comprises a supplementary material.

25. The method of claim 23, wherein step (ii) occurs inside a mammal.

26. The method of claim 23, wherein said implant comprises a biologically active agent.

27. A method of promoting bone growth at a site in need thereof, said method comprising applying to said site the paste of claim 1.

28. The method of claim 27, wherein said site is the surface of an orthopedic implant.

29. The method of claim 27, wherein said site is a bone fracture.

30. The method of claim 27, wherein said paste further comprises a biologically active agent.

31. A method of preparing a structural support for segmented bone, said method comprising contacting bone segments with the paste of claim 1.

32. The method of claim 31, further comprising contacting fixation hardware with said paste.

33. The method of claim 32, wherein said fixation hardware is selected form screws and plates.

* * * * *